United States Patent [19]

Bulley

[11] Patent Number: 4,926,851
[45] Date of Patent: May 22, 1990

[54] TUBULAR BANDAGE AND A METHOD FOR ITS APPLICATION

[75] Inventor: John L. Bulley, St. Columb, United Kingdom

[73] Assignee: JLB Textiles Limited, United Kingdom

[21] Appl. No.: 234,633

[22] Filed: Aug. 22, 1988

[51] Int. Cl.$^5$ .............................................. A61F 15/00
[52] U.S. Cl. .................................... 128/157; 128/155; 128/856
[58] Field of Search ................ 128/155, 157, 165, 856, 128/880, 844; 604/359, 360

[56] References Cited

U.S. PATENT DOCUMENTS

| | | | |
|---|---|---|---|
| 2,123,343 | 7/1938 | Rightsell | 128/157 |
| 2,456,507 | 12/1948 | Hendrickson et al. | 128/157 |
| 3,097,644 | 7/1963 | Parker | 128/157 |
| 3,263,682 | 8/1966 | Rosenfield | 128/157 |
| 3,419,003 | 12/1968 | Kraus et al. | 128/157 |
| 4,674,489 | 6/1987 | Lundy | 128/160 |
| 4,675,014 | 6/1987 | Sustman et al. | 604/375 |
| 4,811,727 | 3/1989 | Etienne | 128/80 R |
| 4,832,010 | 5/1989 | Lerman | 128/165 |

FOREIGN PATENT DOCUMENTS

| | | | |
|---|---|---|---|
| 120908 | 2/1946 | Australia | 128/157 |
| 602653 | 9/1934 | Fed. Rep. of Germany | 128/165 |
| 334123 | 7/1930 | United Kingdom | 128/165 |
| 399591 | 10/1933 | United Kingdom . | |
| 411269 | 6/1934 | United Kingdom . | |
| 412575 | 6/1934 | United Kingdom . | |
| 861977 | 3/1961 | United Kingdom . | |
| 1187018 | 4/1966 | United Kingdom . | |
| 1474300 | 5/1977 | United Kingdom . | |
| 2092006 | 8/1982 | United Kingdom | 604/360 |

*Primary Examiner*—C. Fred Rosenbaum
*Assistant Examiner*—Mark O. Polutta
*Attorney, Agent, or Firm*—Cushman, Darby & Cushman

[57] ABSTRACT

Individual tubular bandages are supplied in rolled form with one end portion rolled outwardly from the free end of the bandage and the other end portion rolled inwardly from the opposite free end so that, in use, a bandage of suitable size may be selected and easily fitted around a body part to be bandaged, the first end being unrolled to cover the body part and the opposite end portion being unrolled to cover the first bandage part. If the body part is an extremity, the central part of the bandage may be twisted to enclose the extremity before the second end portion of the bandage is unrolled.

10 Claims, 2 Drawing Sheets

TUBULAR BANDAGE AND A METHOD FOR ITS APPLICATION

BACKGROUND OF THE INVENTION

The present invention relates to tubular bandages and to a method for their application.

Tubular bandages are in common use and are available in a range of sizes suitable for use in bandaging anything from fingers to arms and legs and even the head. The bandage material is normally supplied in a roll from which a suitable length is cut for use, this length being applied to the injured part to be bandaged with the aid of an applicator.

The application of a bandage with the aid of an applicator is well known and will not therefore be described in detail, but, in brief, first requires the fitting of the length of bandage onto the applicator followed by the fitting of the applicator over the part to be bandaged and its withdrawal to leave one end portion of the bandage around the part. The applicator may then be pushed over the part again and withdrawn several times to apply several thicknesses of the bandage around the injured part.

Although the use of an applicator is not particularly difficult, it does need a certain amount of time and patience and also the thought to replace the applicator with the unused roll of bandage so that they are available for subsequent use. In a busy hospital, this precaution is often omitted and applicators are often lost, which leads to inconvenience, time wastage and irritation. A further problem with such bandages is that a "suitable" length must be cut from the roll for use: often substantially more than is actually needed for a particular job is cut off and considerable quantities of the roll are therefore wasted.

– OBJECT OF THE INVENTION

A particular object of the present invention is to provide a tubular bandage in a more convenient form for applying to an injured part than that described above and to provide an easier method for applying such a bandage.

SUMMARY OF THE INVENTION

Accordingly, the present invention provides a tubular bandage comprising a length of tubular material having a first end portion rolled outwardly from the free end and the other end portion rolled inwardly from the opposite free end to form two rolls each constituted by nearly half the bandage.

The invention also provides a method of applying such a bandage to a body part, including selecting a bandage as described above of a suitable size for the part, fitting the first end portion of the bandage around the body part, adjacent the section to be covered, unrolling the first end portion of the bandage so as to cover the body portion and subsequently unrolling the other end portion of the bandage over the first bandage portion so that the body part is in fact covered by two layers of the tubular bandage.

It will be appreciated that the tubular bandage of the invention is provided in individual units which will normally be cut from a longer, manufactured length of tubular material, such as stockinette. As with current bandage material, the tubular stockinette may be knitted in a range of tube diameters for use on different parts of the body and the lengths cut for the individual bandages of the invention may be gauged fairly accurately to cover the particular body part for which they are intended: this avoids the wastage of material which inevitably occurs when busy nurses have to judge the length required as and when it is needed. By way of example, tubular stockinette having a diameter of about 20mm and a length of approximately 200mm would be suitable for fingers while 60mm diameter tube in lengths of about 500mm would be suitable for forearms.

The provision of the bandages in pre-rolled form considerably facilitates their application to the injured part and avoids any need for an applicator. If the part to be bandaged comprises an extremity, such as a finger, once the first end of the bandage has been rolled into position, the center of the bandage may be twisted, in known manner, before the other end of the bandage is rolled over the first portion so that the finger tip is fully covered. In the case of an intermediate part, such as the forearm however, the bandage would not be twisted in this way.

A bandage unit of the invention is preferably cut so that it is slightly longer than twice the length of the part to be covered so that the free ends of the bandage, when in place, are still slightly rolled: these rolls help to keep the bandage in place although plasters or other means may also be applied to ensure that the bandage is retained. The stockinette currently in use for tubular bandages may be used for the present invention but this known stockinette does not roll easily, has little tendency to return to its original shape after stretching, and tends to unravel from the cut ends. The bandage is therefore preferably made from a knitted fabric incorporating courses of elastic yarn in addition to courses of substantially inelastic yarn. The elastic yarn gives the fabric a certain resilience in addition to that provided by the knitted structure: this makes it easier to roll and, once rolled, helps it remain in its rolled form. Moreover this resilience also enables the fabric to contract slightly around the bandaged part providing radial support and pressure which can assist healing as well as helping to keep the bandage in place, although clearly a bandage must be selected so that it is not so tight as to restrict blood circulation and cause discomfort.

The tubular fabric preferably includes alternate courses of the elastic and inelastic yarns although fabrics may have a greater or lesser proportion of the elastic yarn as convenient for a particular use; the elasticated yarn is, in effect, layed in spirals at predetermined intervals.

The inelastic yarn may comprise any of the spun fiber yarns such as those currently used in bandage materials which are normally cotton, viscose, polyester, cotton/viscose or cotton/polyester mixtures. The elastic yarn may incorporate an elastic filament or may comprise a yarn of the type generally known as a bulked yarn made, for example, from continuous filaments of polyamide or polyester; a bulked yarn may also incorporate an elastic filament.

Bulked yarns provide additional advantages to that of elasticity. In particular, they transmit fluids quickly and easily, are readily washable and dry quickly so that bandages incorporating them may be washed and reused, if necessary, although they would normally be thrown away after a single use. The combination of bulk and resilience of such yarns also makes the fabric knitted from them feel softer and more comfortable in use than the stockinette currently available.

BRIEF DESCRIPTION OF THE DRAWINGS

One embodiment of the invention will now be more particularly described, purely by way of example, with reference to the accompanying drawings in which.

DESCRIPTION OF THE PREFERRED EMBODIMENT

Figure 1:
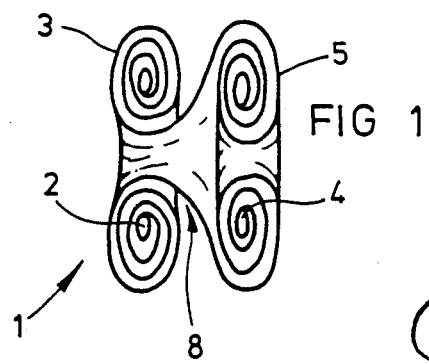
FIG. 1 is a longitudinal sectional view of a bandage according to the invention.

With reference to FIG. 1, a bandage according to the invention is shown in its rolled form and is generally indicated 1. The bandage 1 is, in this case, intended for bandaging a finger and is made from a length of tubular stockinette having a diameter of approximately 20mm and a length of approximately 180mm.

Figure 5:
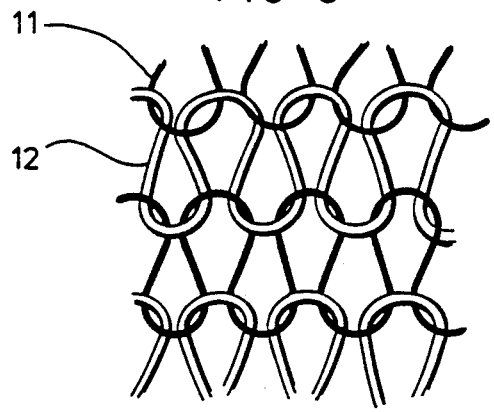
FIG. 5 shows an enlarged detail of part of the fabric of the bandage of FIGS. 1 to 4.

The stockinette fabric from which the bandage 1 is made is plain-knitted on a circular knitting machine and, as seen in the detail of FIG. 5, includes alternate courses of two different yarns 11 and 12, the first yarn 11 being a substantially-inelastic yarn of spun cotton and polyester fibers while the second yarn 12 is an elastic, bulked-NYLON (registered trade mark) yarn.

In FIG. 1, the bandage 1 is shown ready for use and has a first end portion 3 rolled from its free end 2, outwardly on itself, to form the spiral-sectioned roll in the left hand part of FIG. 1. The other end portion of the bandage indicated 5 is, on the other hand, rolled from the opposite free end 4, inwardly of itself, to give the spiral-section roll shown in the right hand part of FIG. 1. The two rolls 3, 5 are each constituted by approximately half the length of the bandage 1.

Figure 2:
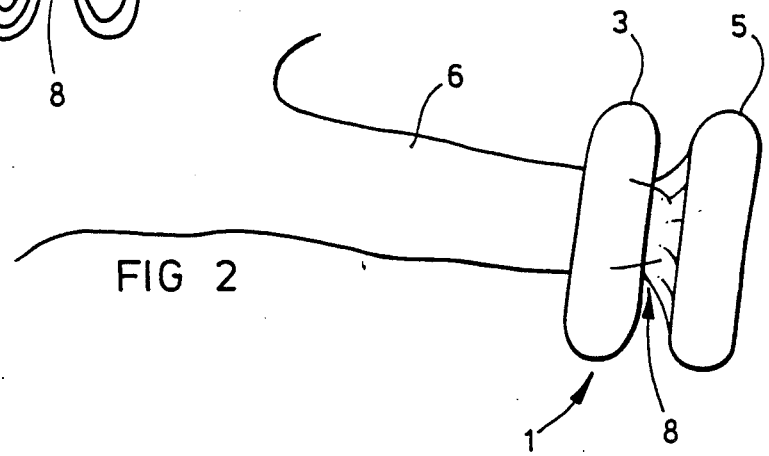
FIGS. 2, 3 and 4 are plan views of the bandage of FIG. 1 in three successive stages of application to a finger.
Figure 3:
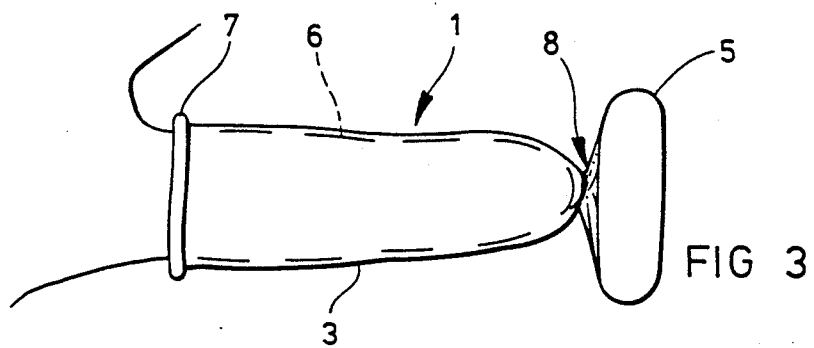
Figure 4:
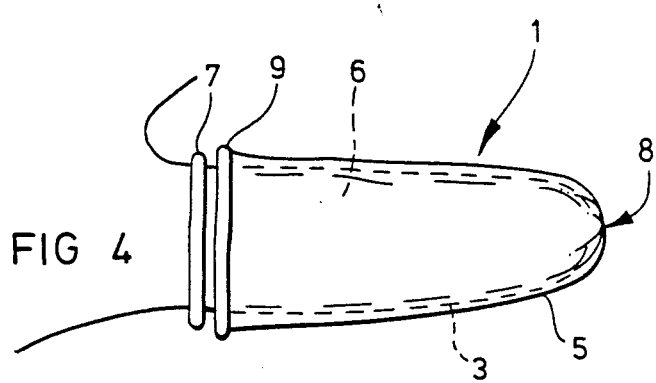

FIGS. 2, 3 and 4 show the use of the bandage 1 in bandaging a finger generally indicated 6.

As shown in FIG. 2, the bandage 1 is first fitted onto the fingertip with the roll 3 surrounding the tip. The roll 3 is then unrolled so as to extend along and around the finger 6, a short end portion indicated 7 remaining in a small roll around the base of the finger to assist in keeping the bandage in place.

At this stage the central part of the bandage, indicated 8, adjacent the finger tip, is twisted as shown in FIG. 3 to close the bandage over the tip.

The other roll 5 is now unrolled along the finger and over the portion 3 already covering the finger. A short end portion 9 is again left in a small roll adjacent the roll 7 and again helps to keep the bandage in place, as shown in FIG. 4. If required, a plaster (not shown) may be applied around the ends 7 and 9 and the base of the finger 6 to keep the bandage 1 in place.

Although the use of a bandage 1 suitable for a finger has been described, similar, but larger, bandages may be provided for other parts of the body and the step of twisting the bandage to close the center may be omitted, if appropriate, or the central part 8 may be tied, either by knotting of the bandage itself or with the aid of an additional thread or tape. Bandages may also be provided in slightly longer lengths so that the ends 7 and 8 can be cut to form ties if required.

The method of application of a bandage to a body part in accordance with the invention and as described above with reference to the drawings may further include the cutting of a length of bandage from a tube and its rolling to the double-spirally rolled form shown in FIG. 1.

It may be noted that, although the bandages 1 are cut from a tubular knitted fabric, they are not prone to unravel from the cut ends since, even if a short length of one yarn is freed, it tends to tangle with the cut end of the other yarn to produce a knot which stops further unravelling. This is a great advantage over ordinary knitted fabrics which are very prone to unravel or run since, as well as reducing wastage, it reduces the irritation caused to the user by such unravelling.

A further extension of the inventive concept of the present invention is the incorporation of a metallised yarn in the bandage fabric. The metal may be integrated in one of the yarns 11 and 12 or in a separate yarn incorporated in the bandage structure.

Bandages made from the fabric may be detectable by metal detectors, such as .those used, for example, in food-production lines to check for foreign bodies in the food produce. In this context, the metallised yarn need contain only 1%-2% by weight of metal, the fabric containing 0.5% by weight or less.

The metal incorporated in a bandage fabric, which must be sterilisable, is preferably stainless steel because of its general inertness although copper or other metals may be used when the requirements in use are less stringent.

What is claimed is:

1. A tubular bandage comprising a length of tubular fabric knitted from a combination of substantially inelastic yarn and elastic yarn so as to have alternating circumferential rows of inelastic yarn and elastic yarn and having a first end portion rolled outwardly from the free end and the other end portion rolled inwardly from the opposite free end to form two rolls each constituted by nearly half the bandage.

2. A tubular bandage as claimed in claim 1, wherein said elastic yarn is selected from bulked, continuous-filament yarns and yarns incorporating a core of elastic material.

3. A tubular bandage as claimed in claim 1, wherein said inelastic yarn is a spun fiber yarn.

4. A tubular bandage as claimed in claim 1, wherein said fabric comprises a plain-knitted stockinette.

5. A tubular bandage as claimed in claim 1, wherein said fabric comprises alternate courses of inelastic yarn and elastic yarn.

6. A tubular bandage as claimed in claim 1, wherein said fabric incorporates a metallised yarn.

7. A tubular bandage as claimed in claim 6, wherein said fabric contains up to approximately 0.5% by weight of metal.

8. A tubular bandage as claimed in claim 7, wherein said metal is stainless steel.

9. A method of applying a bandage to a body part including: selecting a tubular bandage comprising a length of tubular fabric knitted from a combination of substantially inelastic yarn and elastic yarn so as to have alternating circumferential rows of inelastic yarn and elastic yarn and having a first end portion rolled outwardly from the free end and the other end portion rolled inwardly from the opposite free end to form two rolls each constituted by nearly half the bandage, said bandage being of a size suitable for the body part; fitting said bandage around the body with the first rolled end portion adjacent said body part to be bandaged; unrolling said first end portion to cover said body part and subsequently unrolling said other end portion to cover said first end portion and said body part.

10. A method as claimed in claim 9 for bandaging a body extremity, further including, after said unrolling of said first end portion the step of twisting a central portion of said bandage between said end portions so as to close the tube before said unrolling of said other end portion.

* * * * *